United States Patent
Priebe et al.

(10) Patent No.: US 10,481,109 B2
(45) Date of Patent: Nov. 19, 2019

(54) METHOD FOR CHARACTERIZING A SAMPLE COMBINING AN X-RAY CHARACTERIZATION TECHNIQUE AND A SECONDARY IONIZATION MASS SPECTROMETRY CHARACTERIZATION TECHNIQUE

(71) Applicant: COMMISSARIAT A L'ENERGIE ATOMIQUE ET AUX ENERGIES ALTERNATIVES, Paris (FR)

(72) Inventors: Agnieszka Priebe, Grenoble (FR); Guillaume Audoit, Bourgoin Jallieu (FR); Jean-Paul Barnes, Voiron (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 473 days.

(21) Appl. No.: 15/421,660

(22) Filed: Feb. 1, 2017

(65) Prior Publication Data
US 2017/0219502 A1    Aug. 3, 2017

(30) Foreign Application Priority Data
Feb. 2, 2016  (FR) ..................... 16 50811

(51) Int. Cl.
*G01N 23/20*     (2018.01)
*G01N 23/083*    (2018.01)
(Continued)

(52) U.S. Cl.
CPC ..... *G01N 23/20025* (2013.01); *G01N 23/046* (2013.01); *G01N 23/083* (2013.01);
(Continued)

(58) Field of Classification Search
CPC ........... G01N 23/20025; G01N 23/046; G01N 23/083; G01N 23/22014; G01N 23/2258;
(Continued)

(56) References Cited

U.S. PATENT DOCUMENTS

| 5,866,899 A | * | 2/1999 | Hossain | ................. G01N 23/22 |
|---|---|---|---|---|
| | | | | 250/252.1 |
| 2006/0285740 A1 | * | 12/2006 | Okita | .................... G03F 9/7003 |
| | | | | 382/151 |

(Continued)

FOREIGN PATENT DOCUMENTS

WO   WO 2013/035082 A1    3/2013
WO   WO 2014/195998 A1    12/2014

OTHER PUBLICATIONS

Search Report and Written Opinion as issued in French Patent Application No. 1650811, dated Sep. 22, 2016.
(Continued)

*Primary Examiner* — Nicole M Ippolito
(74) *Attorney, Agent, or Firm* — Pillsbury Winthrop Shaw Pittman LLP

(57) ABSTRACT

A method for characterizing a sample combining an X-ray tomography characterization technique and a secondary ionization mass spectrometry characterization technique, includes: a step of providing a tip that includes first and second end surfaces, a first cylindrical region bearing the first end surface and a second region in contact with the first cylindrical region and becoming slimmer towards the second end surface; a step of machining the second region to obtain a sample holder including a flat surface, the flat surface forming an end surface of the sample holder, the area of the flat surface being less than the area of the first end surface; a step of placing the sample on the flat surface of the sample holder; a first step of characterization of the sample using an X-ray characterization technique; a second step of
(Continued)

characterization of the sample using a secondary ionization mass spectrometry characterization technique.

10 Claims, 19 Drawing Sheets

(51) Int. Cl.
| | |
|---|---|
| *H01J 49/00* | (2006.01) |
| *H01J 49/40* | (2006.01) |
| *H01J 49/04* | (2006.01) |
| *G01N 23/20025* | (2018.01) |
| *G01N 23/2204* | (2018.01) |
| *G01N 23/2206* | (2018.01) |
| *G01N 23/2258* | (2018.01) |
| *G01N 23/046* | (2018.01) |

(52) U.S. Cl.
CPC ..... *G01N 23/2204* (2013.01); *G01N 23/2206* (2013.01); *G01N 23/2258* (2013.01); *H01J 49/0072* (2013.01); *H01J 49/0409* (2013.01); *H01J 49/40* (2013.01); *G01N 2223/045* (2013.01); *G01N 2223/0816* (2013.01); *G01N 2223/307* (2013.01)

(58) Field of Classification Search
CPC ..... G01N 2223/045; G01N 2223/0816; G01N 2223/307; H01J 49/0072; H01J 49/0409; H01J 49/40

USPC ............ 250/281, 282, 288, 440.11, 441.11, 250/442.11, 443.1
See application file for complete search history.

(56) References Cited

U.S. PATENT DOCUMENTS

2011/0147578 A1* 6/2011 Schultz .............. G01N 23/2258
250/282
2018/0002806 A1* 1/2018 Verbeck, IV ........... C23C 14/14

OTHER PUBLICATIONS

Bleuet, P., et al., "Specifications for Hard Condensed Matter Specimens for Three-Dimensional High-Resolution Tomographies," Microscopy and Microanalysis, vol. 19, No. 3, Jun. 2013, ISSN: 1431-9276, XP001582238, pp. 726-739.

Behrens, S., et al., "Linking environmental processes to the in situ functioning of microorganisms by high-resolution secondary ion mass spectrometry (NanoSIMS) and scanning transmission X-ray microscopy (STXM)," Environmental Microbiology, vol. 14, No. 11, Mar. 2012, ISSN: 1462-2912, XP055304918, pp. 2851-2869.

* cited by examiner

METHOD FOR CHARACTERIZING A SAMPLE COMBINING AN X-RAY CHARACTERIZATION TECHNIQUE AND A SECONDARY IONIZATION MASS SPECTROMETRY CHARACTERIZATION TECHNIQUE

CROSS-REFERENCE TO RELATED APPLICATIONS

This application claims priority to French Patent Application No. 1650811 filed Feb. 2, 2016, the entire contents of all applications are incorporated herein by reference in their entireties.

TECHNICAL FIELD

The present invention relates to a method for characterizing a sample combining an X-ray characterization technique, for example an X-ray tomography technique, and a secondary ionization mass spectrometry characterization technique, for example a time of flight secondary ionization mass spectrometry technique.

PRIOR ART

When it is wished to analyze a sample, it is known to use an X-ray characterization technique (for example an X-ray tomography technique) or instead a secondary ionization mass spectrometry characterization technique (for example a time of flight secondary ionization mass spectrometry technique). It is also known to use these two techniques in combination. The latter make it possible to analyze small samples and to obtain information such as the crystalline structure or the composition of a sample. However, it remains very difficult to combine these two techniques in an efficient manner.

The X-ray tomography technique is based on the analysis of the phenomenon of diffraction of the X-radiation induced by the sample. The operating principle of this technique is illustrated in FIG. 1. A beam of electrons (1010) strikes a target (1012) which, in reaction, emits an X-radiation (1011). This radiation is then oriented to a sample (300) in rotation and the diffraction pattern is measured using a sensor (1020). It is important that this phenomenon of diffraction is not perturbed by obstacles situated between the source of X-rays (1012) and the sample (300) or instead between the sample (300) and the detector (1020). To reduce these perturbations to the minimum, it is known to arrange the sample (300) on a tip shaped sample holder, the sample (300) being welded to the end of this tip. Thus, the presence of elements around the sample is limited and the diffraction is not affected by perturbations due to the environment.

The secondary ionization mass spectrometry characterization technique consists in subjecting the sample to analyze to an ion beam. The operating principle of this technique is illustrated in FIG. 2. An ion beam (1110) strikes the surface of the sample (300) to analyze which, in reaction, emits ions (1111), said secondary ions. A part of these ions is captured by an extractor (1113) then directed through an electrostatic mirror (1112) to a detector (1120). In order to obtain satisfactory measurement sensitivity, it is important to collect a maximum of these secondary ions (1111). To do so, it is known to resort to a cavity, the sample (300) being arranged in this cavity. In such a configuration, the equipotential field lines induced by the cavity act as a magnifying glass in orienting the secondary ions (1111) to the extractor (1113), improving detection sensitivity accordingly.

If a sample to analyze is arranged on a tip, the X-ray measurement thus takes place in good conditions on account of the absence of obstacles in the vicinity of the sample. However, in the absence of element surrounding the sample, the secondary ions emitted during the step of characterization by secondary ionization mass spectrometry are not oriented to the extractor and the measurement precision is affected by this.

On the contrary, if a sample to analyze is arranged in a cavity, the secondary ionization mass spectrometry measurement becomes more sensitive. However, the X-ray measurement is going to be affected by the cavity situated around the sample and the diffraction pattern will be greatly perturbed, thus affecting the measurement precision.

It will be understood in this case that the requirements concerning the immediate environment of the sample for each of these two techniques are difficult to reconcile. It is thus necessary, when a combined analysis is carried out, to favor one of the two measurements to the detriment of the second.

There thus exists a need to be able to use a characterization method making it possible to carry out a combined analysis while benefiting from maximum sensitivity during the two measurements.

DESCRIPTION OF THE INVENTION

The invention aims to overcome this technical problem by proposing a method for characterizing a sample combining an X-ray characterization technique and a secondary ionization mass spectrometry characterization technique and in which the sample holder has a flat surface making it possible to adapt the environment of the sample in order to obtain better sensitivity for each of the two measurements.

To do so, a first aspect of the invention relates to a method for characterizing a sample combining an X-ray characterization technique and a secondary ionization mass spectrometry characterization technique, and comprising:
  a step of providing a tip, the tip comprising a first end surface, a second end surface, a first cylindrical region bearing the first end surface and a second region in contact with the first cylindrical region and becoming slimmer towards the second end surface;
  a step of machining the second region so as to obtain a sample holder comprising a flat surface, the flat surface forming an end surface of the sample holder, the area of said flat surface being less than the area of the first end surface;
  a step of placing the sample on the flat surface of the sample holder;
  a first step of characterization of the sample using an X-ray characterization technique;
  a second step of characterization of the sample using a secondary ionization mass spectrometry characterization technique.

Cylinder is taken to mean a solid having a lateral wall defined by a straight line known as generator, going through a variable point describing a curve, called guide curve, and maintaining a fixed direction. The curve is preferentially a circle. Alternatively, the curve may be an ellipse or a polygon.

Machining step is taken to mean a step of removal of material. This machining may be carried out by chemical-mechanical planarization, using a diamond saw or a laser beam. Preferably, this machining takes place using an ion beam, this technique enabling good control of the machining as well as a good surface condition after machining.

The flat surface obtained during the implementation of the characterization method is sufficiently small so as not to perturb the X-radiation during the first characterization step. Moreover, the flat surface is sufficiently large to enable an adaptation of the environment of the sample in order to improve sensitivity during the second characterization step. It could be possible for example to install a manipulation structure in order to arrange the sample in a cavity once the first characterization step has been carried out. Alternatively, it could be possible to arrange a structure around the sample in order to increase the sensitivity of the second characterization step. According to another alternative, a cavity could be made at the level of the flat surface in order to arrange the sample therein. Alternatively, a substrate, the latter comprising the sample to analyze surrounded by discrete structures, could be arranged on the flat surface of the sample holder, the discrete structures being laid out so as to improve the sensitivity of the second characterization step.

This method is moreover easy to implement because the tips used to manufacture the sample holder are the tips normally used in X-ray characterization methods.

The characterization method may also have one or more of the following characteristics taken independently or according to any technically possible combinations thereof.

Advantageously, the step of placing the sample comprises:
  a step of machining a first fixation structure on the flat surface of the sample holder;
  a step of placing the sample on the flat surface of the sample holder, at the level of the first fixation structure;
  a step of welding the sample onto the flat surface of the sample holder, at the level of the first fixation structure.

Advantageously, the step of placing the sample also comprises a step of refining the sample, the refining of the sample taking place by machining.

Thus, the correct fixation of the sample is ensured and the latter is no longer liable to move during the step of refining the sample or during the first and second characterization steps. The refining step moreover makes it possible to remove potential adhesive residues present on the sample and to compensate, by machining the sample, any potential incline of said sample relative to the flat surface of the sample holder.

Advantageously, the method comprises, after the first characterization step and before the second characterization step:
  a step of machining, in a first substrate separate from the sample holder, a cavity, said measurement cavity;
  a step of machining a second fixation structure, close to the first fixation structure, on the flat surface of the sample holder;
  a step of placing a manipulation structure on the flat surface of the sample holder at the level of the second fixation structure;
  a step of welding the manipulation structure onto the flat surface of the sample holder, at the level of the second fixation structure;
  a step of machining a part of the flat surface of the sample holder so as to free a region comprising the first and second fixation structures and thus form a second sample holder;
  a step of placing the second sample holder, using the manipulation structure, in the measurement cavity made on the first substrate.

The sample may thus be displaced using the manipulation structure, that is to say without being manipulated directly, and thus see its environment modified between the two measurements. During the first characterization step, the sample is located on the flat surface of the sample holder and the absorption of X-radiation is then minimal. On the other hand, during the second characterization step, the sample is located in a cavity, which increases measurement sensitivity on account of better extraction of secondary ions, the cavity acting as a magnifying glass by reorienting the secondary ions to the extractor.

Alternatively, the method comprises, after the first characterization step and before the second characterization step;
  a step of machining, in a second substrate separate from the sample holder, a first orifice;
  a step of machining, around the first orifice, a structure of dimensions substantially equal to those of the flat surface of the sample holder, so as to obtain a first element pierced by an orifice;
  a step of placing the first element pierced by an orifice on the flat surface of the sample holder such that the sample is situated in the orifice of said first element;
  a step of welding the first element pierced by an orifice to the flat surface of the sample holder;
the orifice forming a measurement cavity around the sample.

Thus, during the first characterization step, the sample is located on the flat surface of the sample holder and the absorption of X-radiation is then minimal. On the other hand, during the second characterization step, the sample is located in the orifice of the first element which acts as a cavity.

Alternatively, the method comprises, after the first characterization step and before the second characterization step, a step of charged particle beam assisted deposition of a structure surrounding the sample, the structure forming a measurement cavity around the sample.

Thus, during the first characterization step, the sample is located on the flat surface of the sample holder and the absorption of X-radiation is therefore low. On the other hand, during the second characterization step, the sample is located in the structure surrounding the sample which acts as a cavity.

Advantageously, the deposited structure is of cylindrical shape. This embodiment is particularly suited when the sample has the shape of a cylinder because in this case, the walls of the structure are at equal distance from the sample at all points, which improves the extraction of secondary ions during the second characterization step. Alternatively, the deposited structure is half-cylindrical.

Alternatively, the sample holder is transparent to X-rays and the method further comprises, after the step of machining the flat surface and before the step of placing the sample, a step of machining a cavity; the sample being arranged in this cavity during the placing step, such that the cavity forms a measurement cavity around the sample.

Thus, during the first characterization step, the low thickness and the choice of the material composing the sample holder are such that the absorption of X-radiation remains very low. In addition, during the second characterization step, the sample is still located in the cavity which, as described previously, increases measurement sensitivity on account of better extraction of secondary ions, the cavity acting as a magnifying glass. Advantageously, when the sample is welded to the sample holder using the first fixation structure, the first fixation structure is situated at the bottom of the measurement cavity.

Advantageously, the distance $d_{s-c}$ between the sample and the walls of the measurement cavity are given by:

$$d_{s-c} = h_s \cdot \tan(\alpha)$$

where $h_s$ is the height of the sample, tan is the tangent function and $\alpha$ is the incidence angle of the ion beam relative to the normal of the surface of the sample holder.

This distance makes it possible to reduce the shading effect induced by the walls of the measurement cavity during the second characterization step while maintaining the effect of orientation of the secondary ions through the measurement cavity.

Alternatively, the step of placing the sample comprises:
- a step of providing a third substrate separate from the sample holder;
- a step of placing the sample on the third substrate;
- the production, around the sample, of discrete structures, the height of the structures being equal to the height of the sample;
- a step of placing the third substrate on the flat surface of the sample holder;
- a step of welding the third substrate onto the flat surface of the sample holder;
- the dimensions of the third substrate being chosen such that the totality of the third substrate rests on the flat surface of the sample holder.

Advantageously, the distance $d_{s-c}$ separating the discrete structure the closest to the sample from the sample itself is given by:

$$d_{s-c} = h_s \cdot \tan(\alpha)$$

where $h_s$ is the height of the sample, tan is the tangent function and $\alpha$ is the incidence angle of the ion beam relative to the normal of the surface of the sample holder.

BRIEF DESCRIPTION OF THE FIGURES

Other characteristics and advantages of the invention will become clearer from reading the detailed description that follows, and by referring to the appended figures, which illustrate.

For greater clarity, identical or similar elements are marked by identical reference signs in all of the figures.

DETAILED DESCRIPTION OF AT LEAST ONE EMBODIMENT

Figure 1:
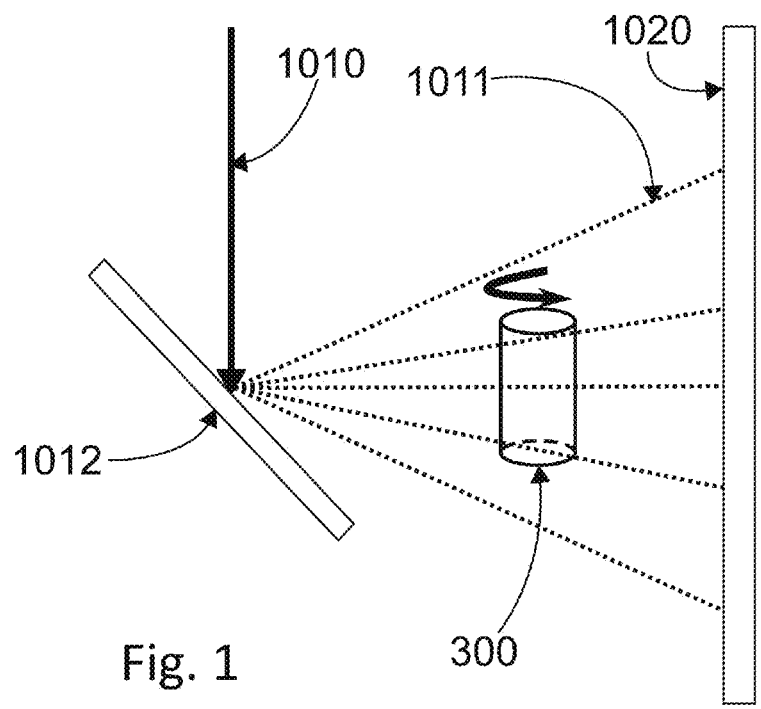
FIG. 1, an operating principle of an X-ray characterization method.
Figure 2:
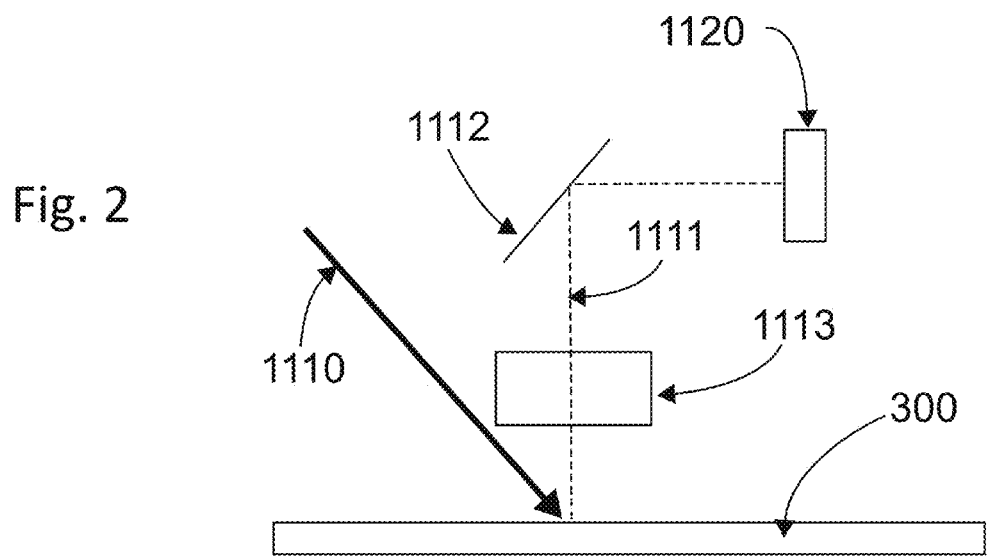
FIG. 2, an operating principle of a secondary ionization mass spectrometry characterization method.
Figure 3:
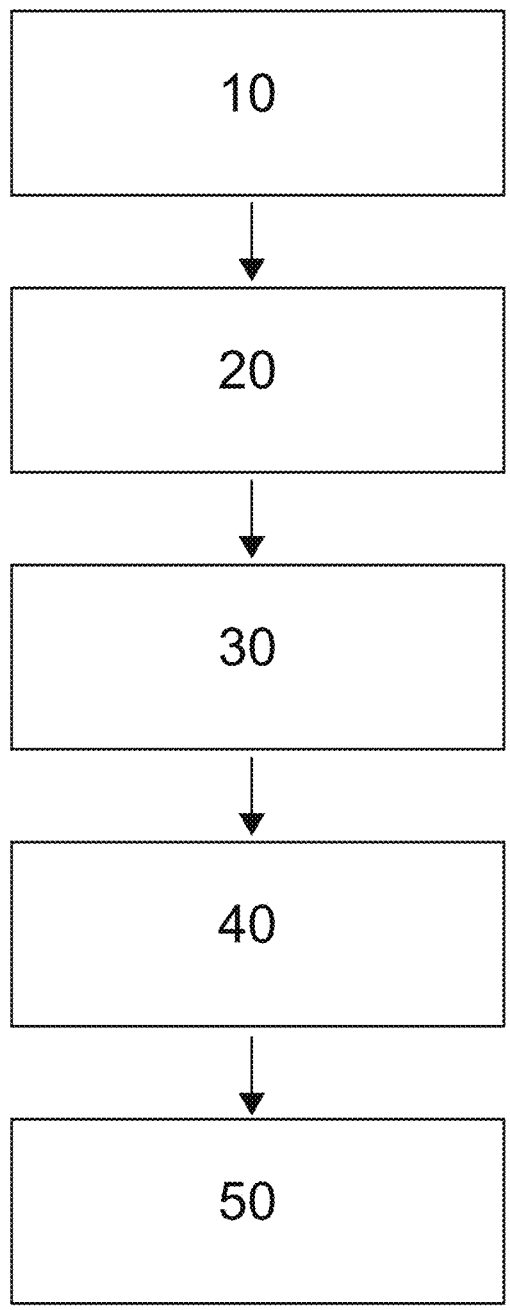
FIGS. 3, 4 and 5, a first embodiment of the invention.
Figure 4:
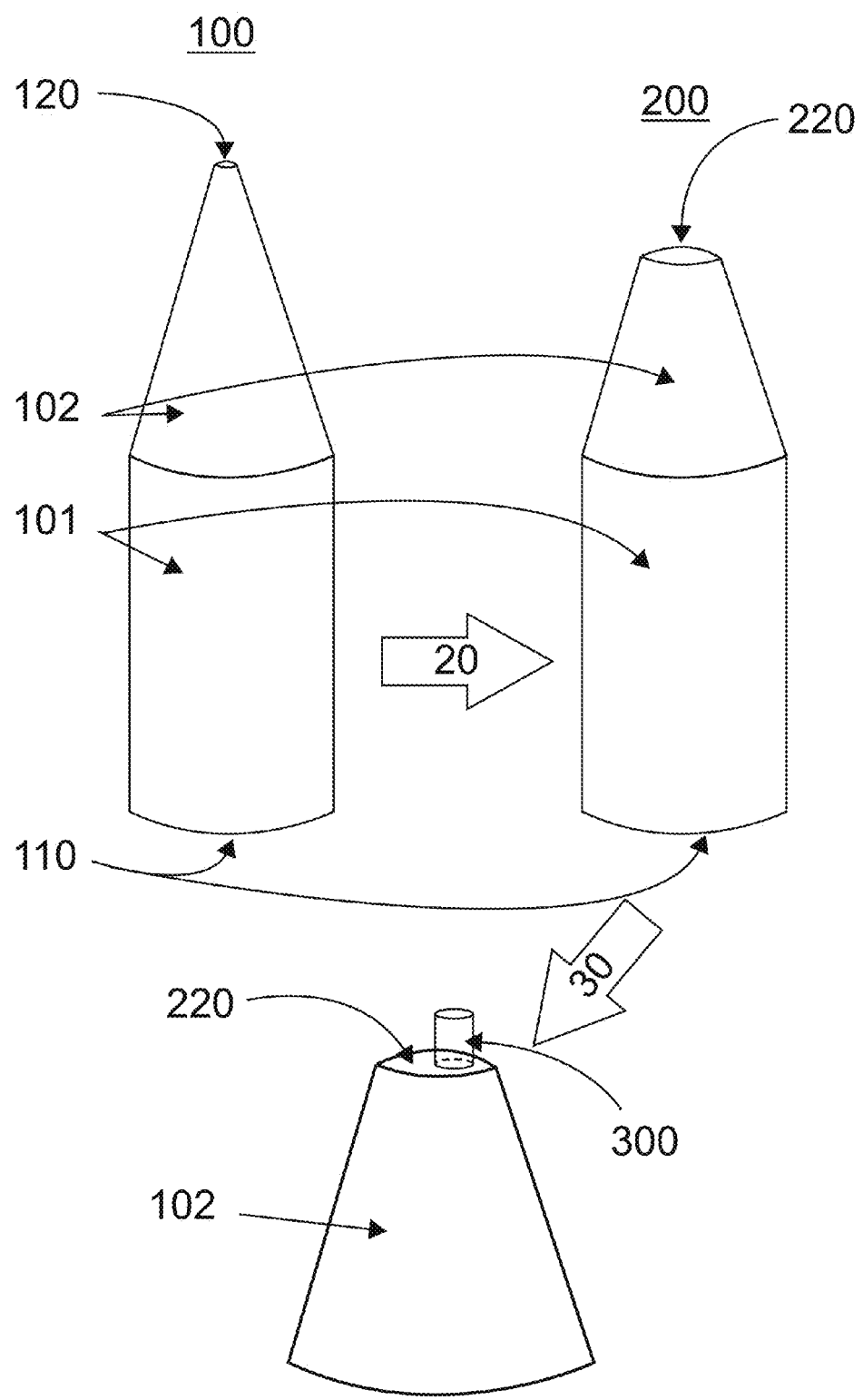

In a first embodiment illustrated in FIGS. 3 and 4, the method for characterizing a sample (300) combining an X-ray characterization technique such as an X-ray tomography technique and a secondary ionization mass spectrometry characterization technique such as a time of flight secondary ionization mass spectrometry technique comprises a step of providing (10) a tip (100), the tip (100) comprising a first end surface (110), a second end surface (120), a first cylindrical region (101) bearing the first end surface (110) and a second region (102) in contact with the first cylindrical region (101) and becoming slimmer towards the second end surface (120).

The method also comprises a step of machining (20) the second region (102) so as to obtain a sample holder (200) comprising a flat surface (220), the flat surface (220) forming an end surface of the sample holder (200), the area of said flat surface (220) being less than the area of the first end surface (110); a step of placing (30) the sample (300) on the flat surface (220) of the sample holder (200); a first step of characterization (40) of the sample (300) using an X-ray characterization technique; a second step of characterization (50) of the sample (300) using a secondary ionization mass spectrometry characterization technique.

The tip used (100) to manufacture the sample holder (200) may be manufactured by a method known to those skilled in the art or purchased commercially.

Preferably, the diameter of the tip (100) at the level of the second end surface (120) is comprised between 50 and 100 µm, or even substantially equal to 80 µm. Preferably, its diameter is chosen such that, after machining, the flat part (220) of the sample holder (200) has a diameter comprised between 100 and 1000 µm. The use of a flat surface (220) of small size makes it possible to limit the phenomenon of absorption during the first characterization step (40), which consists in an X-ray characterization. Moreover, the flat surface (220) obtained is sufficiently large to enable an arrangement of the environment of the sample (300) in such a way as to make the second characterization step (50), which consists in a secondary ionization mass spectrometry characterization, more sensitive. This adaptation of the environment may take place between the first characterization step (40) and the second characterization step (50) but also before the first characterization step, on condition of limiting the absorption of X-rays.

As described hereafter, a manipulation structure could for example be installed in order to arrange the sample in a cavity once the first characterization step has been carried out. Alternatively, a structure could be arranged around the sample in order to increase the sensitivity of the second characterization step. According to another alternative, a cavity could be made at the level of the flat surface in order to arrange the sample therein. Alternatively, a substrate, the latter comprising the sample to analyze surrounded by discrete structures, could be arranged on the flat surface of the sample holder, the discrete structures being laid out so as to improve the sensitivity of the second characterization step.

In order to obtain the desired planeness, the machining is carried out according to an angle normal to the cylindrical region (101). It may be carried out by chemical-mechanical planarization, using a diamond saw or by a laser technique for example. Preferably, the machining is carried out using an ion beam, this technique enabling finer control of the cutting angle, with a precision of the order of 0.5°.

The first X-ray characterization step may consist in an X-ray tomography characterization step. The second characterization step (50), which consists in a secondary ionization mass spectrometry characterization, is a destructive characterization technique and thus has to take place last in the characterization method that is the subject matter of the invention. The technique for detecting secondary ions is preferentially a time of flight measurement detection technique.

Figure 5:
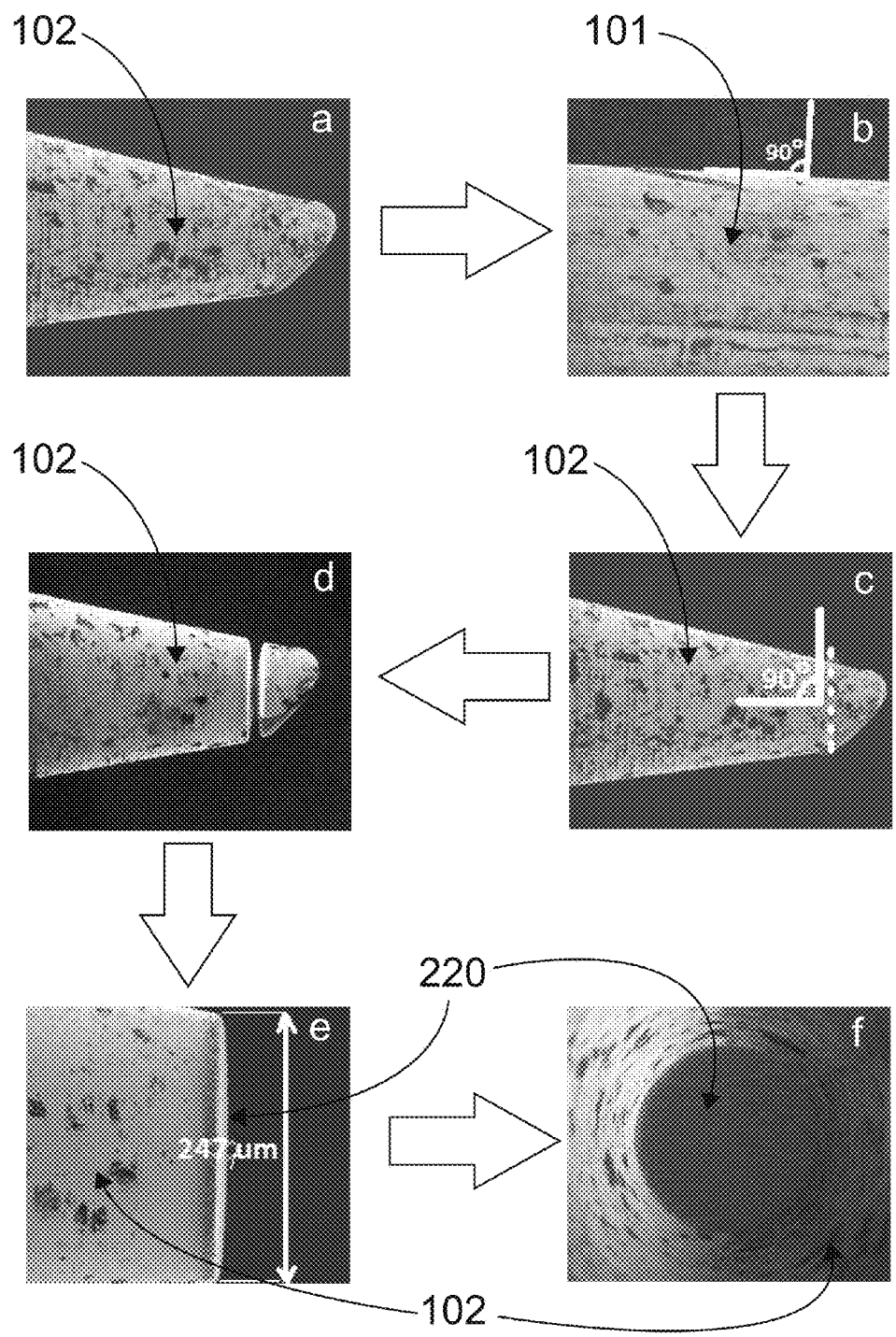

In an example illustrated in FIG. 5, in order to obtain the sample holder (200), firstly a tip is provided (FIG. 5a). The normal to the first cylindrical region (101) of the tip (FIG. 5b) is then measured and the angle obtained is transferred to the second region (102) of the tip (FIG. 5c). A machining using an ion beam (FIG. 5d) is then carried out in order to obtain a flat surface (FIGS. 5e and 5f). In the embodiment illustrated in FIG. 5e, the diameter of the flat part is substantially equal to 250 µm.

The sample (300) may be obtained by a conventional sample preparation technique. The sample may for example be of square shape with a width comprised between 35 µm and 100 µm, or even substantially equal to 60 µm. Alternatively, the sample may be of cylindrical shape and its diameter comprised between 35 µm and 100 µm, for example substantially equal to 60 µm. The sample may have a height comprised between 50 and 100 µm, for example substantially equal to 70 µm.

Figure 6:
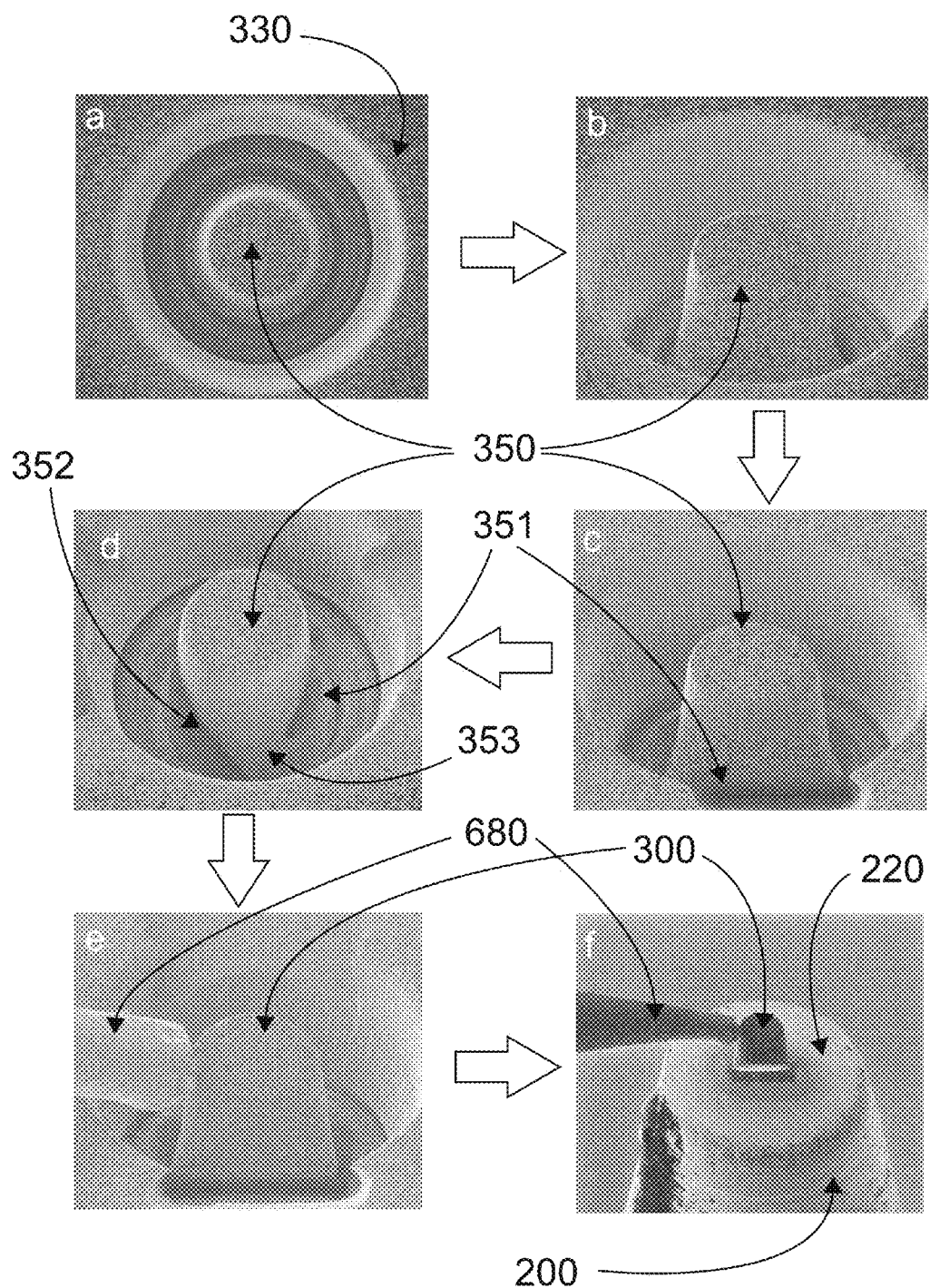
FIG. 6, the preparation of the sample.

The sample may be machined using an ion beam technique. In one embodiment illustrated in FIG. 6, during a first step (FIGS. 6a and 6b), a first cylinder (350) is defined in a substrate (330) composed of the material to analyze. In a second step (FIG. 6c), the ion beam is inclined in order to make a cut (351) in a first part of the cylinder (350). The angle of inclination of the beam is preferably substantially equal to 45° relative to the surface of the substrate. Then a second cut (352) is made (FIG. 6d) in a manner opposite to the first cut (351), along an angle identical to the first cut, only leaving an anchoring point (353) between the cylinder and the remainder of the substrate. The presence of this anchoring point prevents the first cylinder (350) from falling during the complete cut of the structure. Then, a micromanipulator (680) is coupled (FIG. 6e) to the cylinder (350) then a final cut is made along an angle identical to the first cut in order to free the cylinder from the remainder of the substrate so as to define a sample (300). The micromanipulator may be coupled by a welding technique. It is possible for example to use a charged particle beam assisted deposition technique. The material used may for example be platinum. In a final step (FIG. 6f), the sample is deposited on the flat surface (220) of the sample holder (200). The micromanipulator is then detached from the sample in order to be able to conduct the characterization steps. The detachment of the sample may be obtained by an ion beam machining technique.

Figure 7:
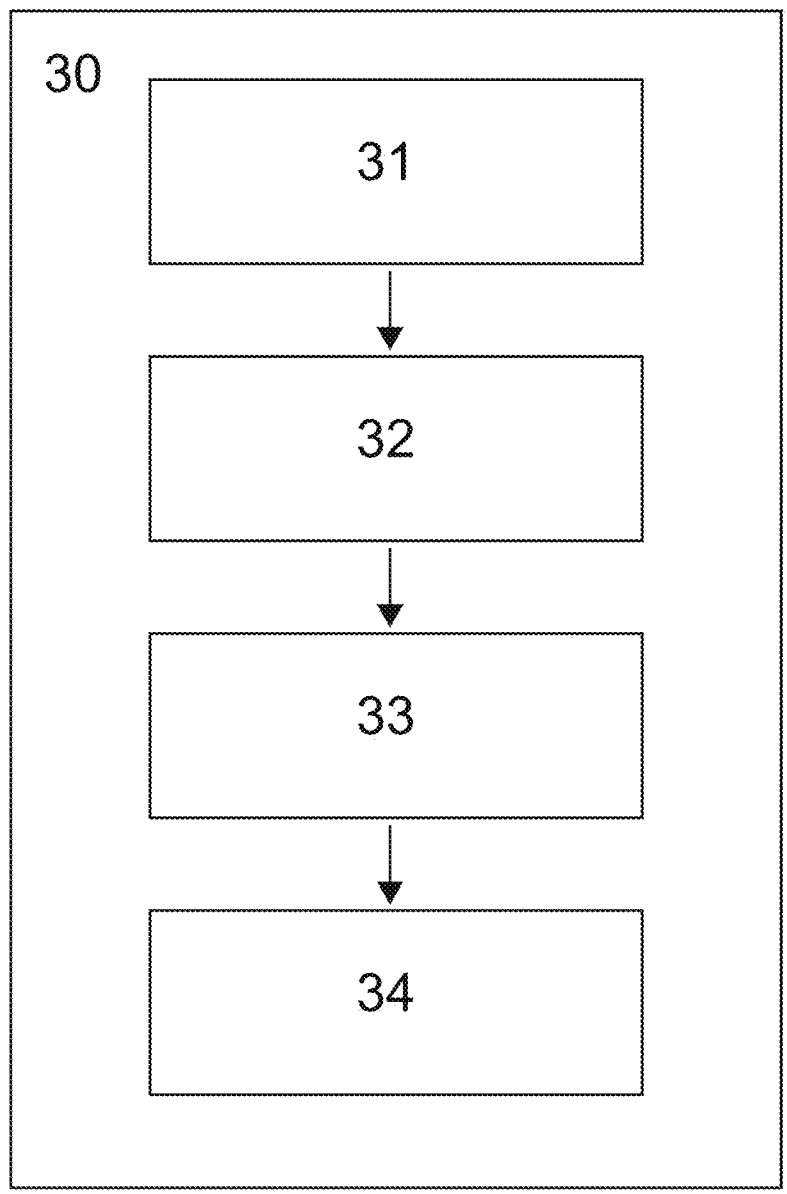
FIGS. 7, 8 and 9, a second embodiment of the invention.
Figure 8:
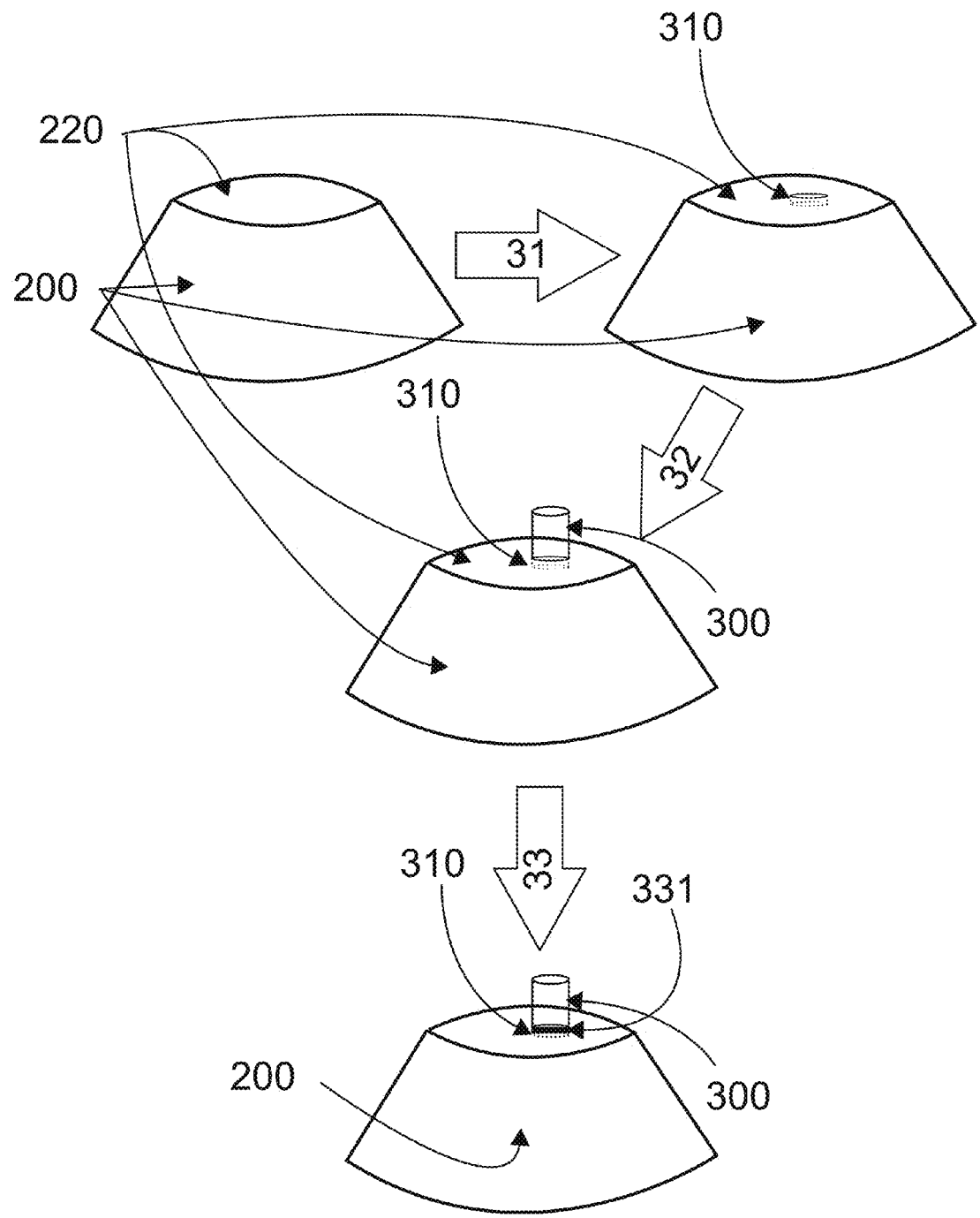

In a second embodiment illustrated in FIGS. 7 and 8, the step of placing (30) the sample (300) comprises a step of machining (31) a first fixation structure (310) on the flat surface (220) of the sample holder (200); a step of placing (32) the sample (300) on the flat surface (220) of the sample holder (200) and; a step of welding (33) the sample (300) onto the flat surface (220) of the sample holder (200), at the level of the first fixation structure (310).

In one embodiment, the step of placing (30) the sample (300) also comprises a step of refining (34) the sample (300), the refining of the sample (300) taking place by machining.

Thus, the sample (300) is integral with the sample holder (200) and is not liable to move during the characterization steps but especially during the refining step (34). The refining step (34) further makes it possible to remove potential residues of adhesive present on the sample (300) and to compensate, by machining the sample (300), any potential incline of said sample (300) relative to the flat surface (220) of the sample holder (200).

The first fixation structure (310) may take the form of a trench or a cavity on the surface of the flat part (220) into which a part of the sample (300) to analyze is going to be inserted. The geometry of this structure is fixed by the geometry of the sample (300) to analyze.

The step of welding (33) the sample (300) onto the first fixation structure (310) may be carried out through charged particle beam assisted deposition (331). The welding may for example be carried out with platinum.

Figure 9:
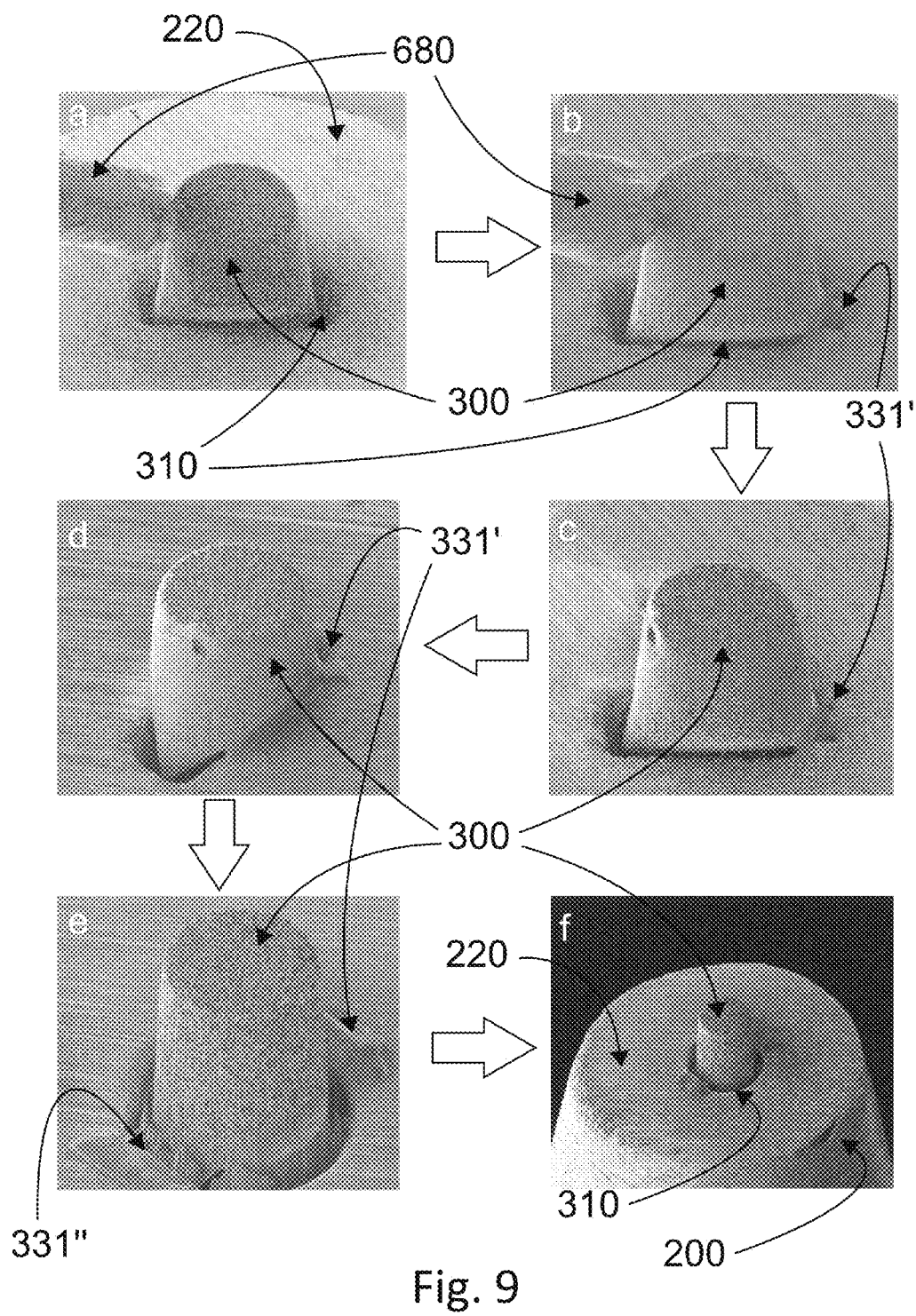

The placing (30) of the sample (300) may take place using a micromanipulator (680) as illustrated in FIG. 9. In one embodiment, a first step (FIG. 9a) consists in placing the base of the sample (300) in the first fixation structure (310). The micromanipulator (680) may be attached to the sample (300) by a welding technique. Once the sample (300) is in place, a first welding point (331') is produced (FIG. 9b) at the junction between the sample (300) and the first fixation structure (310). This welding (331') may for example be carried out during a step of charged particle beam assisted deposition. Once the sample (300) has been made integral with the flat surface (220) of the sample holder (200), the micromanipulator (680) may be detached (FIG. 9c) from the sample (300) without there being a risk of the sample (300) falling. The first welding point (331') may then be reinforced by carrying out a new deposition of material (FIG. 9d). A second welding point (331") is produced at the junction between the sample (300) and the first fixation structure (310) in order to reinforce the fixation (FIG. 9e). The sample (300) is thus integral (FIG. 9f) with the first fixation structure (310) and thus with the sample holder (200).

Figure 10:
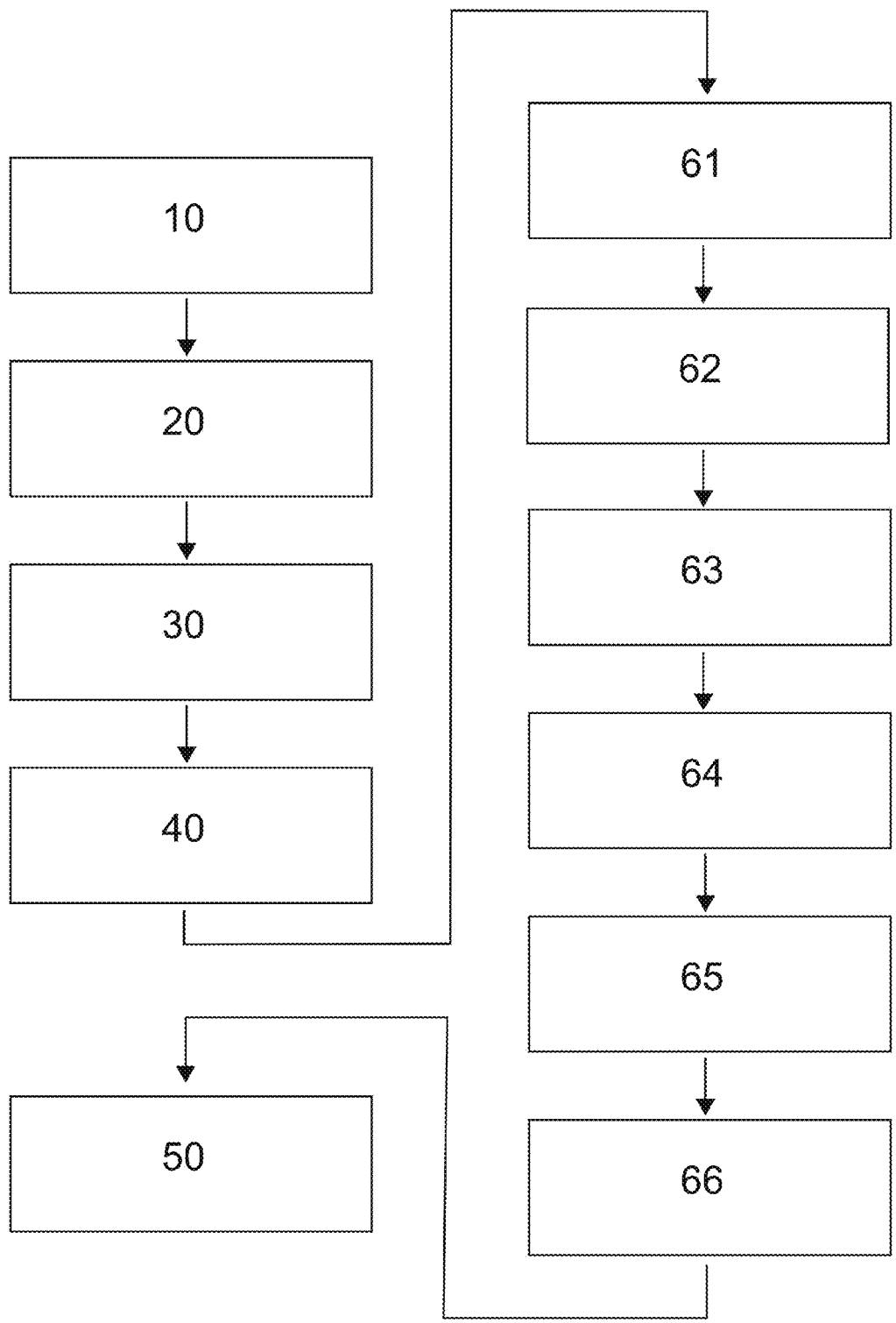
FIGS. 10, 11 and 12, a third embodiment of the invention.
Figure 11:
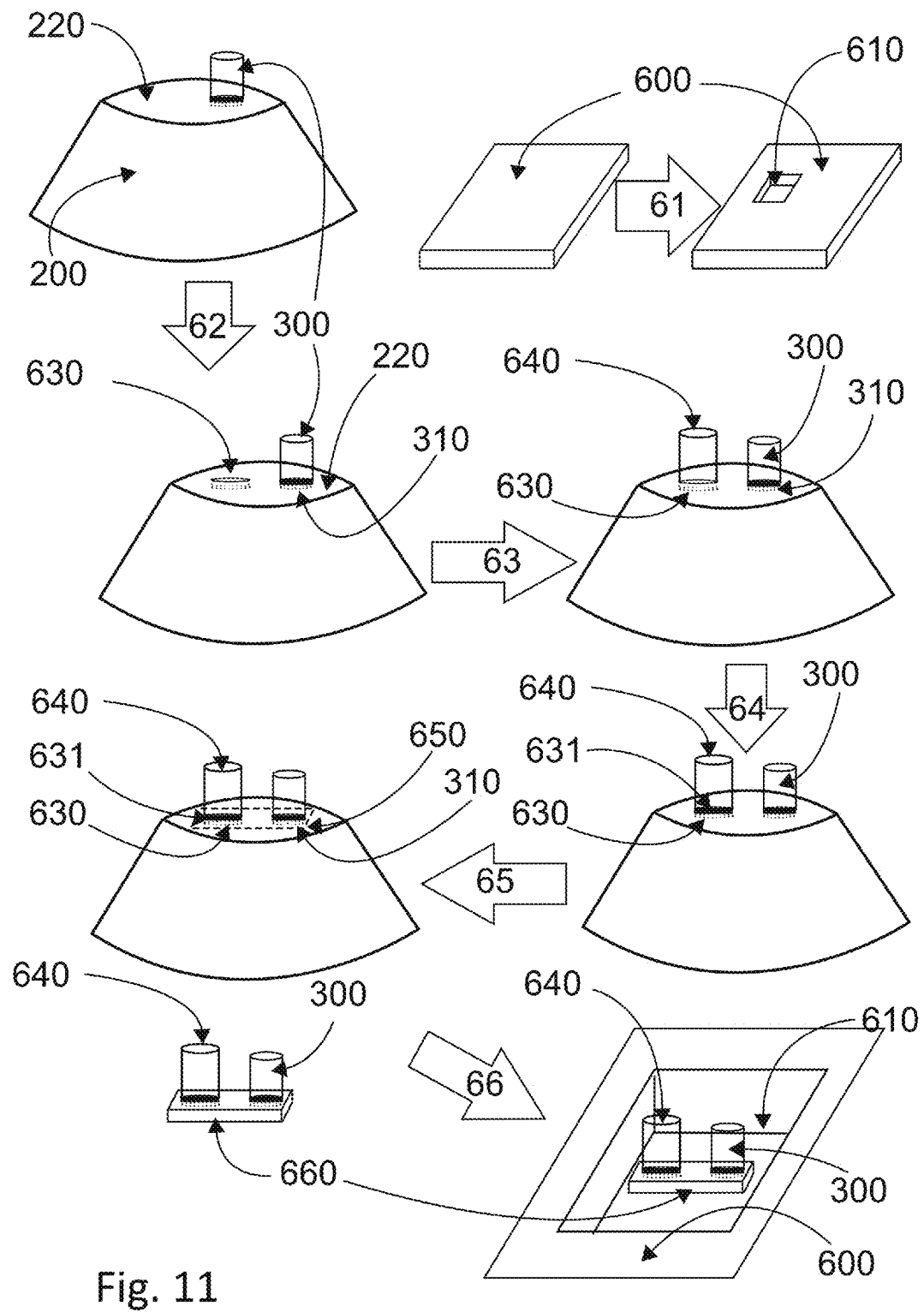

In a third embodiment illustrated in FIGS. 10 and 11, the method comprises, after the first characterization step (40) and before the second characterization step (50), a step of machining (61), in a first substrate (600) separate from the sample holder, a cavity (610), said measurement cavity; a step of machining (62) a second fixation structure (630), close to the first fixation structure (310), on the flat surface (220) of the sample holder (200); a step of placing (63) a manipulation structure (640) on the flat surface (220) of the sample holder (200) at the level of the second fixation structure (630); a step of welding (64) the manipulation structure (640) onto the flat surface (220) of the sample holder (200), at the level of the second fixation structure (630); a step of machining (65) a part of the flat surface (220) of the sample holder (200) so as to free a region (650) comprising the first (310) and second fixation structures (630) and thus form a second sample holder (660) and; a step of placing (66) the second sample holder (660), using the manipulation structure (640), in the cavity (610) made on the first substrate (600).

The installation of the manipulation structure (640) is made possible by the particular shape of the sample holder (200) and in particular by the flat surface (220) produced at the step of machining (20) the tip (100). This manipulation structure (640) makes it possible to manipulate the sample (300) without touching it directly which avoids the latter being damaged between the first characterization step (40) and the second characterization step (50).

Figure 12:
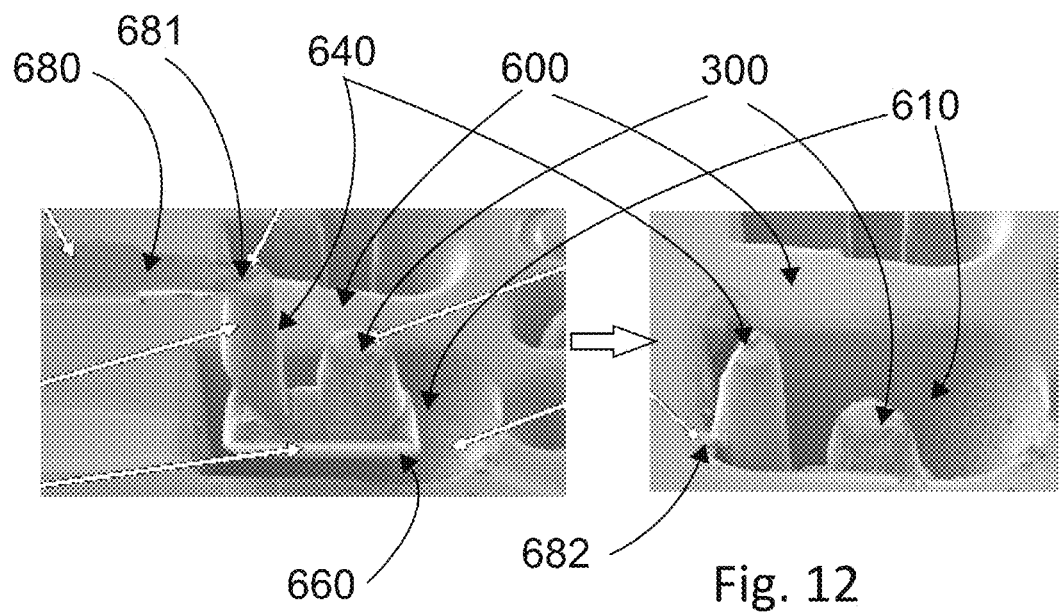

The step of placing the second sample holder in the cavity may take place using a micromanipulator (680) as illustrated in FIG. 12. Firstly, the micromanipulator (680) is coupled by welding (681) to the manipulation structure (640). Since the manipulation structure (640) is integral with the second sample holder (660), the latter may be extracted from the sample holder (200) in order to be arranged in the cavity (610) produced in the first substrate (600). The depth of the cavity (610) of the first substrate (600) is thus fixed by the height of the manipulation structure (640). In fact, if the cavity (610) is too deep, the micromanipulator (682) is going to enter into contact with the first substrate (600) before the second sample holder (660) has touched the bottom of the cavity (610) and the second sample holder (660) could not be put in place correctly in this cavity (610). Preferably, the depth of the cavity (610) does not exceed the height of the manipulation structure (640). It is however possible to create a trench in order to make a passage for the micromanipulator in the substrate (600). Preferably, once in place in the cavity (610), a welding (682) is carried out between the substrate (600) and the manipulation structure (640) in order to make the second sample holder (660) integral with the substrate (600).

Preferably, the first substrate (600) is constituted of a conductor material which avoids the phenomenon of charge during the second characterization step (50). Alternatively, the first substrate (600) is constituted of an insulator material and a step of deposition of a conductor layer is carried out before placing (66) the second sample holder (660) in the cavity (610). Preferably, the first substrate (600) is a silicon substrate.

The cavity (610) produced in the first substrate (600) may be obtained by an ion beam machining technique. In one embodiment, the cavity (610) machined in the first substrate (600) is of rectangular shape. Its length may be comprised between 150 and 450 µm, preferably substantially equal to 350 µm. Preferably, the width of the cavity (610) is comprised between 150 and 350 µm, preferably substantially equal to 250 µm.

The second fixation structure (630) may adopt a shape similar to the first fixation structure (310), that is to say take the shape of a trench or a cavity. The step of welding the manipulation structure (640) onto the fixation structure (630) may take place through charged particle beam assisted deposition (631).

The manipulation structure (640) may take the shape of a cylinder and be obtained using a technique similar to the technique used to manufacture the sample (300). Preferably, the manipulation structure is made of silicon.

Advantageously, the height of the manipulation structure (640) is substantially equal to or greater than the height of the sample (300). The height of the manipulation structure (640) may for example be comprised between 150 and 250 µm, or even substantially equal to 180 µm. The diameter of the manipulation structure (640) is then substantially equal to 50 µm and the distance between the manipulation structure (640) and the sample (300) is comprised between 20 and 70 µm, or even substantially equal to 50 µm.

In one embodiment, the second sample holder (660) is of rectangular shape. Preferably, the width of the second sample holder (660) is comprised between 50 and 100 µm, preferably substantially equal to 75 µm and the length of the sample holder is comprised between 100 and 300 µm, preferably substantially equal to 200 µm. Preferably, the manipulation structure (640) and the sample (300) are aligned in the sense of the length of the second sample holder (660).

Once the second sample holder (660) is in place in the cavity (610), it is preferable that the sense of the length of the second sample holder (660) is parallel to the sense of the length of the cavity (610).

Figure 13:
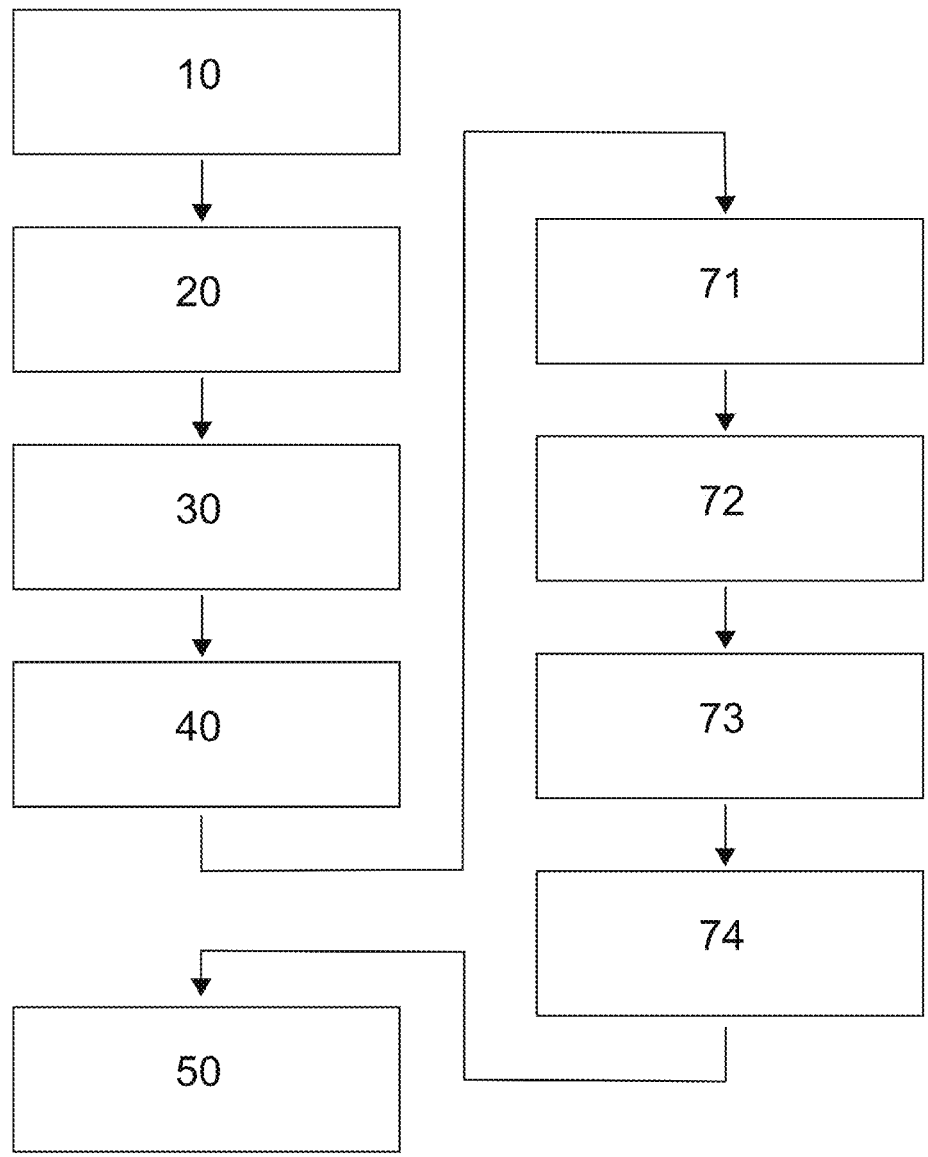
FIGS. 13 and 14, a fourth embodiment of the invention.
Figure 14:
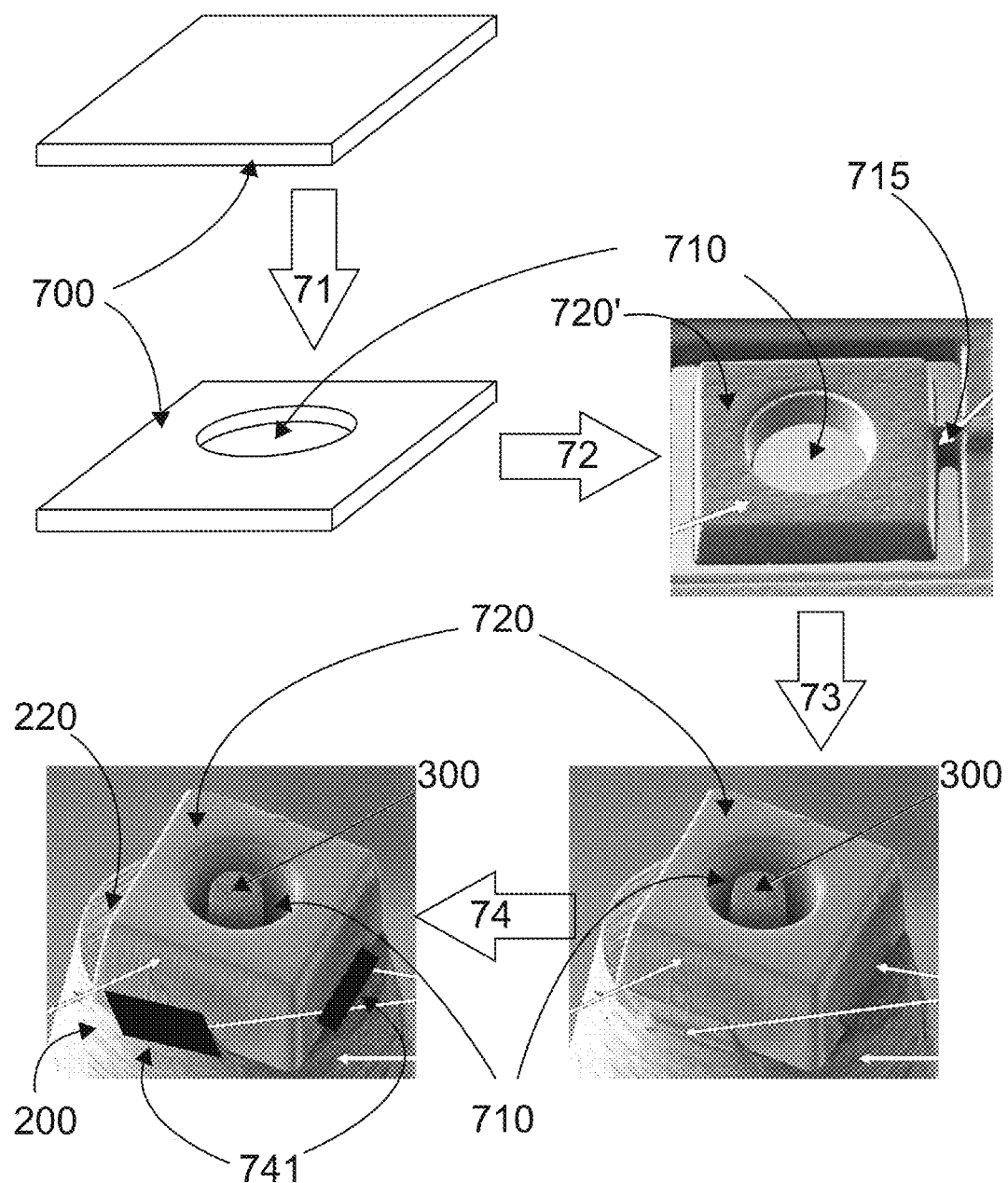

In a fourth embodiment illustrated in FIGS. 13 and 14, the method according to the invention comprises, after the first characterization step (40) and before the second characterization step (50), a step of machining (71), in a second substrate (700) separate from the sample holder (200), a first orifice (710); a step of machining (72), around the first orifice, a first structure (720') and of dimension substantially equal to the flat surface (220) of the sample holder (200), so as to obtain a first element (720) pierced by an orifice (710); a step of placing (73) the first element (720) pierced by an orifice (710) on the flat surface (220) of the sample holder (200) such that the sample (300) is situated in the orifice (710) of said first element (720); a step of welding (74) the first element (720) pierced by an orifice (710) onto the flat surface (220) of the sample holder (200). Thus, the first element (720) pierced by an orifice (710) produces a measurement cavity around the sample (300).

In this embodiment, it is then preferable to choose a sample (300) of cylindrical shape, the symmetry thus obtained enabling better confinement of the field lines and thus higher efficiency in the recovery of secondary ions during the second characterization step (50).

Preferably, the machining of the orifice (710) takes place along a direction normal to the surface of the second substrate (700). In one embodiment, the diameter of the orifice (710) is comprised between 90 and 100 µm. In this case, a diameter of the sample (300) comprised between 35 and 45 µm could for example be chosen.

Preferably, during the step of machining (72) the structure (720'), a supporting bridge (715) is left. This supporting bridge (715) enables the structure (720') to not detach from the substrate (700). A micromanipulator is then attached to the structure (720') by welding. Once the micromanipulator has been made integral with the structure (720'), the supporting bridge (715) is eliminated. The micromanipulator then makes it possible to arrange the first element (720) pierced by its orifice (710) thus obtained around the sample (300). The first element (720) may have any shape. Preferably, as illustrated in FIG. 14, the first element (720) is of square shape.

Preferably, the thickness of the second substrate (700) is substantially equal to the height of the sample (300). In one embodiment, the thickness of the second substrate (700) is comprised between 50 and 100 µm and the first element (720) may adopt a square shape of which the width is substantially equal to 180 µm.

The material of the substrate (700) may be insulator or conductor. In the case of an insulator substrate (700), resort could be made to a deposition of metal material in order to avoid a phenomenon of charge during the second characterization step (50). Preferably, the second substrate (700) is made of silicon.

Preferably, during the step of placing the first element (720) around the sample (300), an observation is carried out by placing oneself above the sample (300) so as to be able to align easily the orifice (710) of the first element (720) with the sample (300) to analyze and thus to ensure the correct placement of the sample (300) in the orifice (710).

Preferably, the step of welding (74) the first element (720) onto the flat surface (220) of the sample holder (200) may take place through charged particle beam assisted deposition (741). The material deposited is for example platinum.

Figure 15:
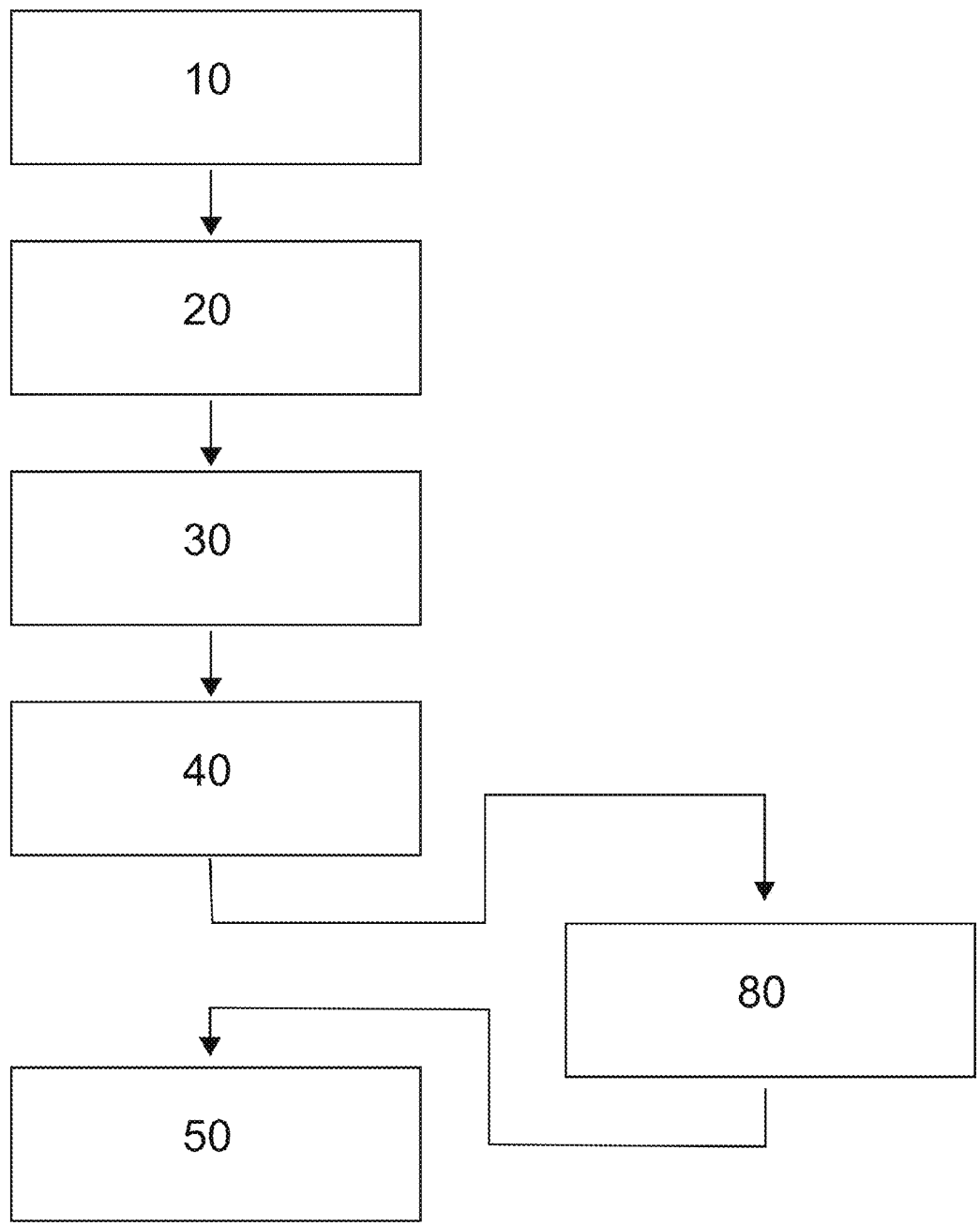
FIGS. 15 and 16, a fifth embodiment of the invention.
Figure 16:
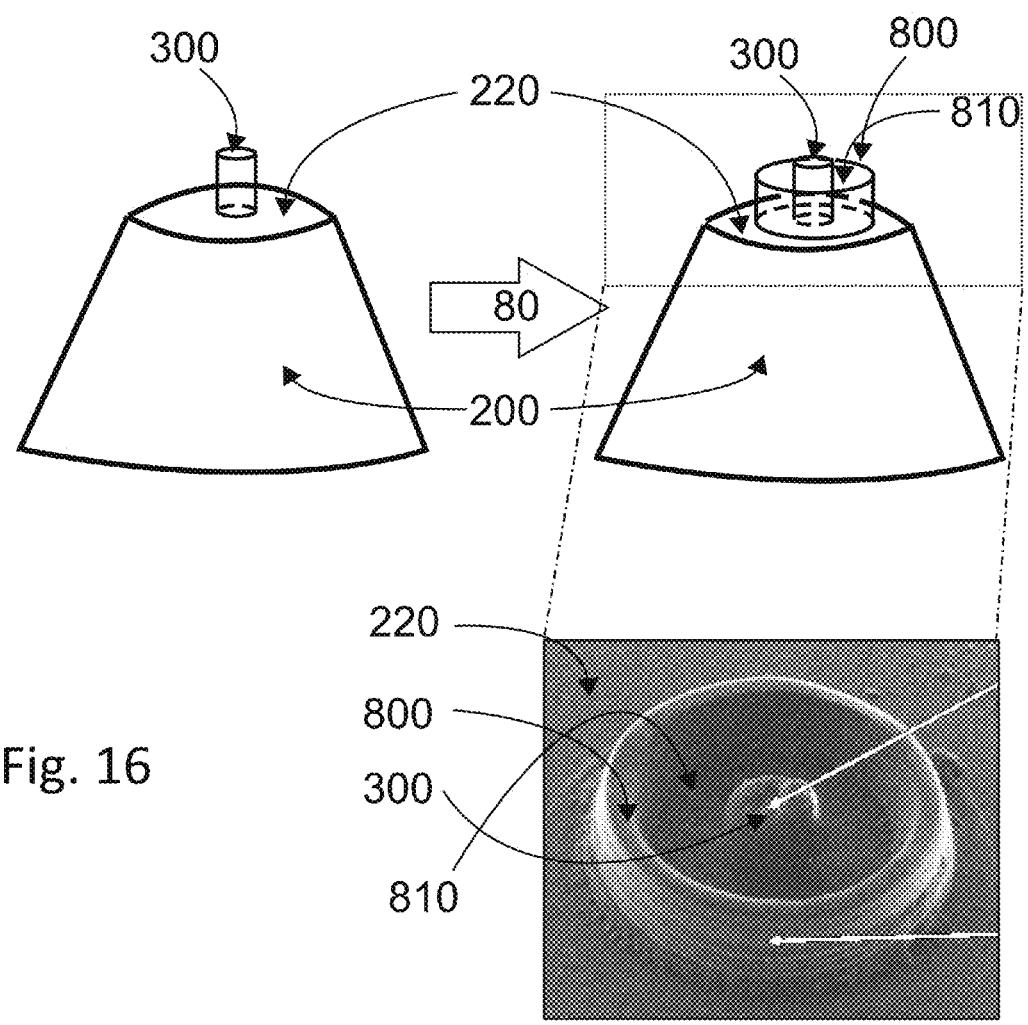

In a fifth embodiment illustrated in FIGS. 15 and 16, the method comprises after the first characterization step (40) and before the second characterization step (50), a step of charged particle beam assisted deposition (80) of a structure (800) surrounding the sample (300), the structure (800) forming a cavity (810) around the sample (300) playing the role of measurement cavity.

Alternatively, the deposition step (80) is carried out before the first characterization step (40). In this case, the material deposited to form the structure (800) is transparent to X-rays. In this embodiment, it is preferable to choose a thickness of the walls of the structure sufficiently large to avoid collapse of the latter but sufficiently narrow so as not to attenuate the X-radiation in a too significant manner. It is thus necessary to take into account the absorption coefficient of the material used to produce the structure.

In the exemplary embodiment illustrated in FIG. 16, the width of the structure is substantially equal to 340 µm, the height of the structure is substantially equal to 110 µm and the thickness of the walls of the structure is substantially equal to 35 µm, the structure being produced by a deposition of $SiO_2$ from a III/HMCHS (2,4,6,8,10,12-hexamethylcyclohexasiloxane) precursor. Generally speaking, any material with low atomic number, and thus easily absorbing X-rays, may be used.

Preferably, the structure (800) and the sample (300) have a cylindrical shape. The cylindrical shape has the advantage of producing better confinement of the lines of electrostatic fields, and thus greater capacity for recovering secondary ions emitted during the second characterization step.

Alternatively, the structure (800) may have the shape of a half-cylinder, the center of the half-cylinder being merged with the center of the sample (300). This embodiment is particularly suited when the deposition of the structure takes place before the first characterization step (40). In fact, due to the half-cylindrical shape, the absorption of X-rays is more limited, a single wall located on the path of the X-radiation during the first characterization step (40). In the embodiment corresponding to a half-cylindrical structure, the height of the walls of the structure (800) is chosen substantially equal to the height of the sample (300) or even slightly greater, for example greater than 10%, than the height of the sample.

Figure 17:
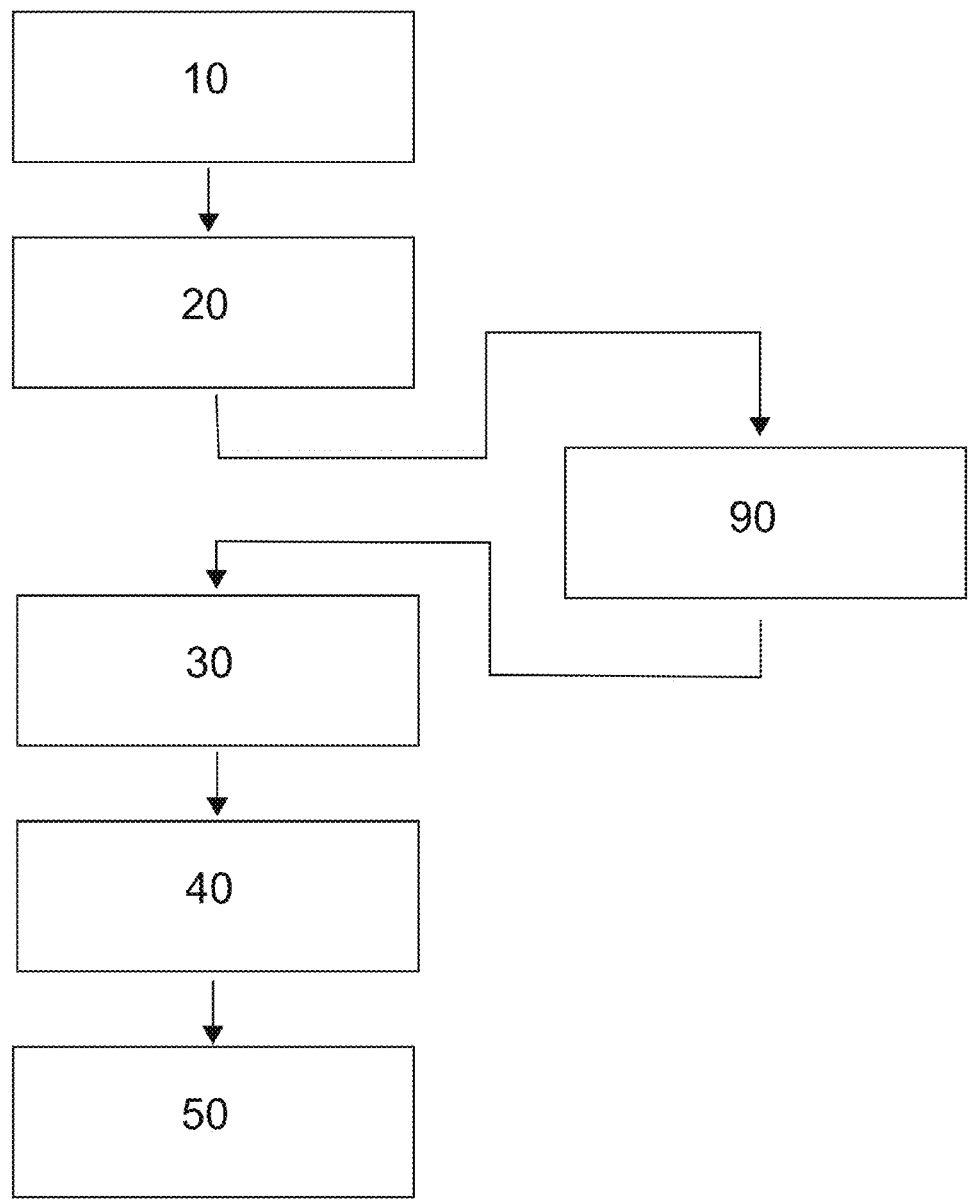
FIGS. 17 and 18, a sixth embodiment of the invention.
Figure 18:
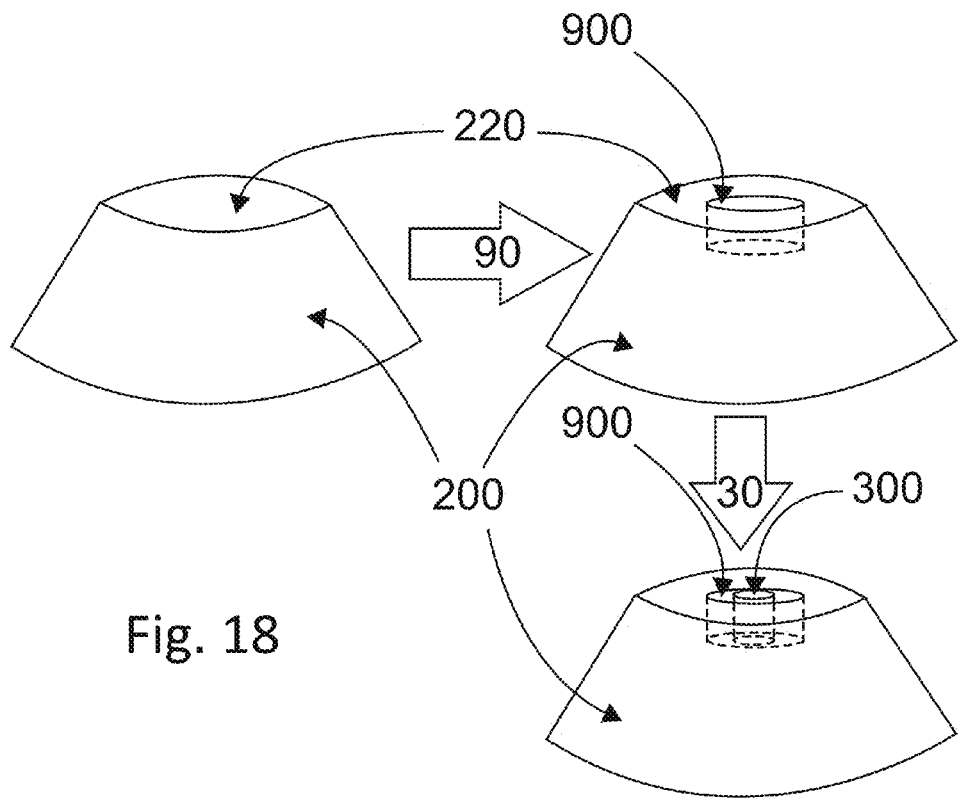

In a sixth embodiment illustrated in FIGS. 17 and 18, the method comprises, after the step of machining (20) the flat surface (220) and before the step of placing the sample (30), a step of machining (90) a cavity (900); the sample being arranged in this cavity during the placing step (30), so as to form a measurement cavity around the sample.

The cavity (900) is preferably obtained using a machining by ion beam. Preferably, the ion beam used for the machining is oriented perpendicularly to the flat surface of the sample holder.

Preferably, the material used to manufacture the sample holder (200) is transparent to X-rays. Particular attention must be paid to the choice of this material and not just the thickness of the walls of the cavity (900) but also the coefficient of absorption of the material used must be taken into account. The material may notably be selected from materials with low atomic number Z such as quartz, lithium, beryllium, graphite or instead a polymer (such as poly methyl methacrylate (PMMA)). If the material chosen is an insulator, a step of deposition of a thin conducting layer is carried out in order to avoid the phenomenon of charge during the second characterization step (50). This deposition step must be carried out before placing the sample in the cavity in order that the deposited material does not interfere with the signal of the sample (300). Nevertheless, if the signal contrast between the conducting material deposited and the sample (300) measured is sufficiently high, this deposition step may take place while the sample (300) is already in place in the cavity (900).

Figure 20:
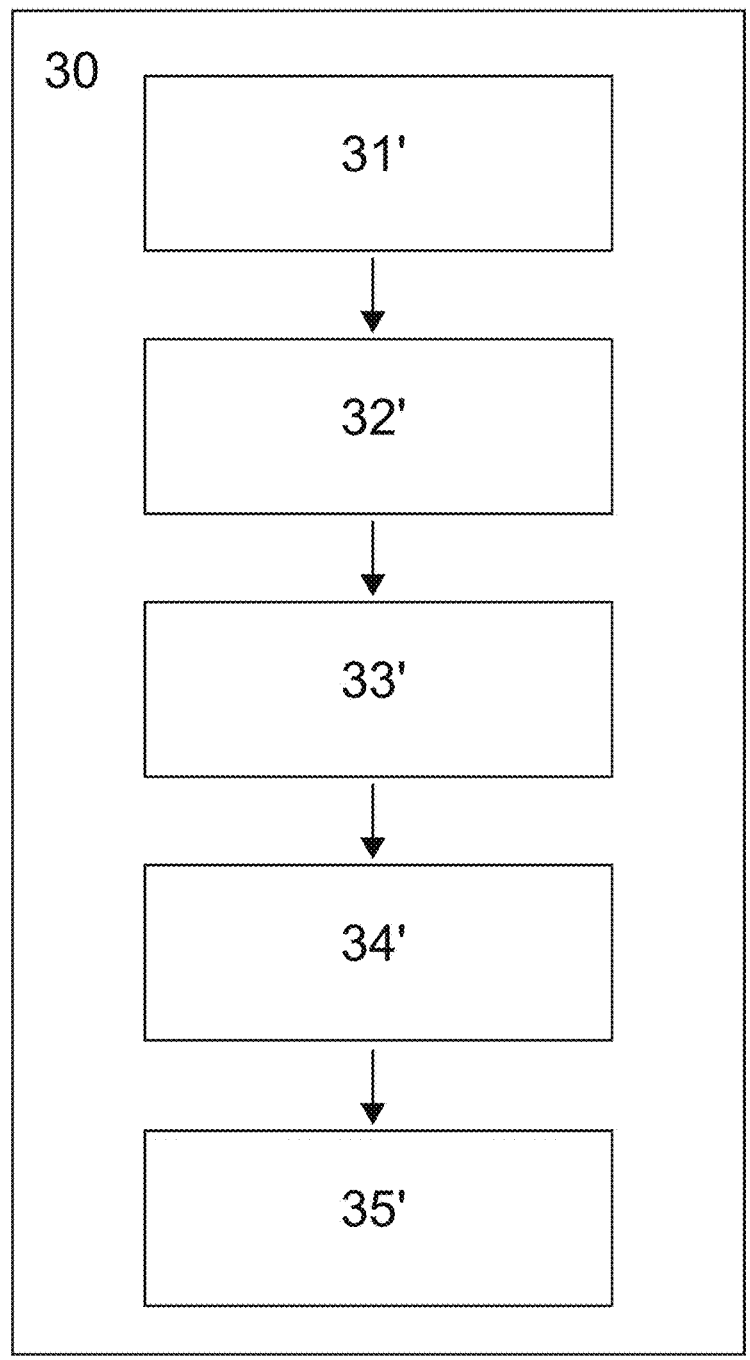
FIGS. 20 and 21, a seventh embodiment of the invention.
Figure 21:
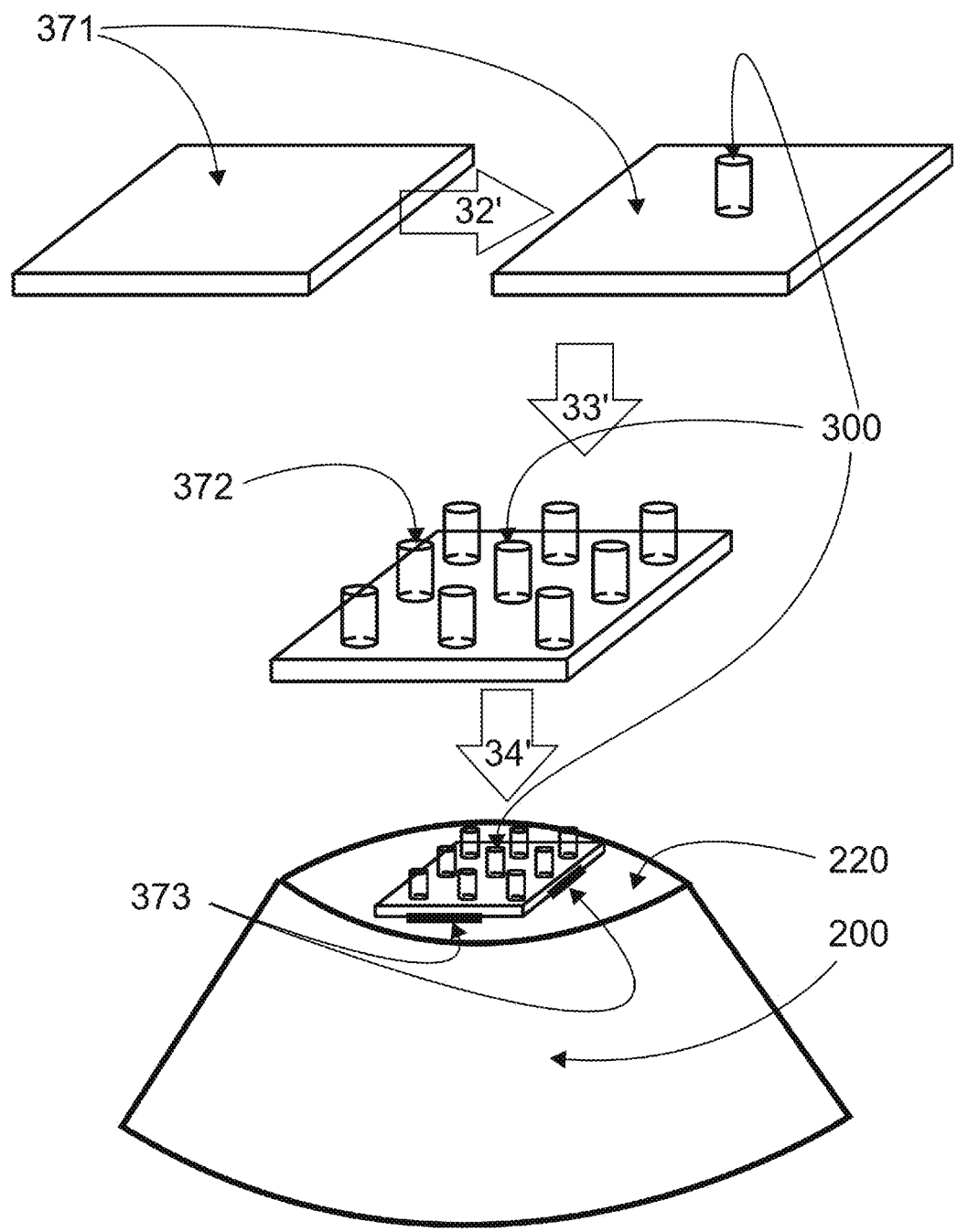

In a seventh embodiment illustrated in FIGS. 20 and 21, the step of placing (30) the sample (300) comprises a step of providing (31') a third substrate (371) separate from the sample holder (200); a step of placing (32') the sample on the third substrate (371); the production (33'), around the sample (300), of discrete structures (372) of cylindrical shape, the height of the discrete structures (372) being equal to the height of the sample (300); a step of placing (34') the third substrate (371) on the flat surface of the sample holder (200); a step of welding (35') the third substrate (371) onto the flat surface (220) of the sample holder (200); the dimensions of the third substrate (371) being chosen such that the totality of the third substrate (371) rests on the flat surface (220) of the sample holder (200).

Preferably, the discrete structures (372) are of cylindrical shape. Preferably, the third substrate (371) is of square shape. Alternatively, the third substrate (371) is of cylindrical shape. Preferably, the step of welding (35') the third substrate (371) onto the flat surface (220) of the sample holder (200) may take place through charged particle beam assisted deposition (373). The material used is for example platinum.

Figure 19:
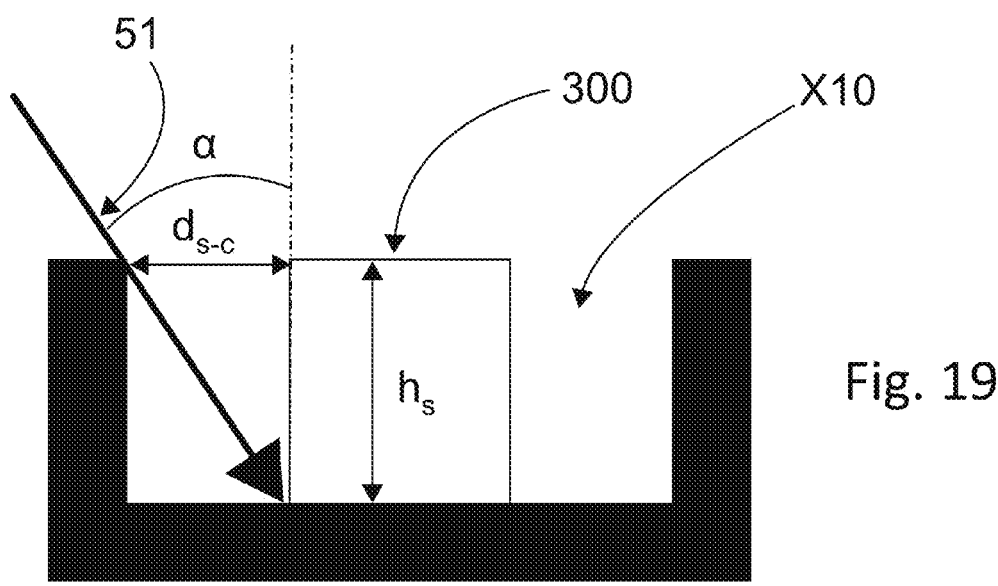
FIG. 19, the phenomenon of shading.

As illustrated in FIG. 19, in the embodiments described previously, the structures arranged around the sample make it possible to define a measurement cavity (X10). However, the walls of this cavity may hinder the path of the ion beam (51) during the second characterization step (50), said beam not being able to access the lowest part of the sample (300). This phenomenon is known by the name of shading. In order to limit this shading effect as much as possible it is therefore advisable to choose the correct distance $d_{s-c}$ separating the sample (300) from the walls of the measurement cavity (X10). This distance is given by the expression:

$$d_{s-c} = h_s \cdot \tan(\alpha)$$

where $h_s$ is the height of the sample, tan is the tangent function and $\alpha$ is the incidence angle of the ion beam (51) relative to the normal of the surface of the sample holder. This expression assumes that the depth of the cavity (X10) is substantially identical to the height of the sample (300).

The respect of this distance influences the quality of the second characterization step (50). In fact, if the distance separating the walls of the cavity (X10) of the sample (300) is too great, the influence of the cavity (X10) on the secondary ions becomes too weak and the quality of the measurement during the second characterization step (50) is degraded. On the contrary, if the distance is too small, the beam does not have access to the lower part of the sample (300) and the analysis of the latter thus takes place in an incomplete manner.

In the embodiment illustrated in FIGS. 10, 11 and 11, the distance $d_{s-c}$ is fixed by the dimensions of the manipulation structure (640), and in particular its width, and by the distance separating the manipulation structure (640) from the sample (300). In this embodiment, when it is specified that the second fixation structure (630) is close to the first fixation structure (310), it is understood that the distance separating the first fixation structure from the second fixation structure is such that, when the sample (300) is in the cavity (610), the distance $d_{s-c}$ respects the previously established relation.

In the embodiment illustrated in FIGS. 13 and 14, the depth of the cavity (710) should be understood as the height of the structure pierced by an orifice.

In the same way, in the embodiment illustrated in FIGS. 15 and 16, the depth of to the cavity (810) should be understood as the height of the structure obtained by growth.

In the embodiment illustrated in FIGS. 20 and 21, the cavity is in fact constituted of discrete structures that act in a similar manner on the field lines, that is to say that their presence contributes to the orientation of the ions emitted in the direction of the extractor. The depth of the cavity must thus be understood as being the height of the discrete structures and the distance $d_{s-c}$ correspond to the distance separating the discrete structure the closest to the sample from the sample itself.

The invention claimed is:

1. A method for characterizing a sample combining an X-ray tomography characterization technique and a secondary ionization mass spectrometry characterization technique, the method comprising:
   a step of providing a tip, the tip comprising a first end surface, a second end surface, a first cylindrical region bearing the first end surface and a second region in contact with the first cylindrical region and becoming slimmer towards the second end surface;
   a step of machining the second region so as to obtain a sample holder comprising a flat surface, the flat surface forming an end surface of the sample holder, an area of said flat surface being less than an area of the first end surface;
   a step of placing the sample on the flat surface of the sample holder;
   a first step of characterization of the sample using an X-ray characterization technique;
   a second step of characterization of the sample using a secondary ionization mass spectrometry characterization technique.

2. The method according to claim 1, wherein the step of placing the sample comprises:
   a step of machining a first fixation structure on the flat surface of the sample holder;
   a step of placing the sample on the flat surface of the sample holder, at the level of the first fixation structure;
   a step of welding the sample onto the flat surface of the sample holder, at the level of the first fixation structure.

3. The method according to claim 2, further comprising, after the first characterization step and before the second characterization step:
   a step of machining, in a first substrate separate from the sample holder, a cavity, said measurement cavity;
   a step of machining a second fixation structure, close to the first fixation structure, on the flat surface of the sample holder;
   a step of placing a manipulation structure on the flat surface of the sample holder at the level of the second fixation structure;
   step of welding the manipulation structure onto the flat surface of the sample holder, at the level of the second fixation structure;
   a step of machining a part of the flat surface of the sample holder so as to free a region comprising the first and second fixation structures and thus form a second sample holder;
   a step of placing the second sample holder, using the manipulation structure, in the measurement cavity made on the first substrate.

4. The method according to claim 3, wherein a distance $d_{s-c}$ between the sample and walls of the measurement cavity is given by:

$$d_{s-c} = h_s \cdot \tan(\alpha)$$

where $h_s$ is a height of the sample, tan is a tangent function and $\alpha$ is an incidence angle of an ion beam relative to the flat surface of the sample holder.

5. The method according to claim 2 wherein the first fixation structure is situated at the bottom of the measurement cavity.

6. The method according to claim 1, further comprising, after the first characterization step and before the second characterization step:
   a step of machining, in a second substrate separate from the sample holder, a first orifice;
   a step of machining, around the first orifice, a structure of dimensions substantially equal to those of the flat surface of the sample holder, so as to obtain a first element pierced by an orifice;
   a step of placing the first element pierced by an orifice on the flat surface of the sample holder such that the sample is situated in the orifice of said first element;
   a step of welding the first element pierced by an orifice onto the flat surface of the sample holder;
   the orifice forming a measurement cavity around the sample.

7. The method according to claim 1, further comprising, after the first characterization step and before the second characterization step, a step of charged particle beam assisted deposition of a structure surrounding the sample, the structure forming a cavity, said measurement cavity, around the sample.

8. The method according to claim 7, wherein the deposited structure is of half-cylindrical or cylindrical shape.

9. The method according to claim 1, wherein the material of the sample holder is transparent to X-rays and wherein the method further comprises, after the step of machining the flat surface and before the step of placing the sample, a step of machining a cavity; the sample being arranged in said cavity during the placing step, such that the cavity forms a measurement cavity around the sample.

10. The method according to claim 1, wherein the step of placing the sample comprises:
   a step of providing a third substrate separate from the sample holder;
   a step of placing the sample on the third substrate;
   the production, around the sample, of discrete structures, the height of the structures being equal to the height of the sample;
   a step of placing the third substrate on the flat surface of the sample holder;
   a step of welding the third substrate onto the flat surface of the sample holder;
   the dimensions of the third substrate being chosen such that the totality of the third substrate rests on the flat surface of the sample holder.

* * * * *